United States Patent
Stankowski et al.

(10) Patent No.: US 7,378,017 B2
(45) Date of Patent: *May 27, 2008

(54) DISPOSABLE FLUID SEPARATION DEVICE AND MANIFOLD ASSEMBLY DESIGN WITH EASY CHANGE-OUT FEATURE

(75) Inventors: Ralph Stankowski, Westford, MA (US); J. Karl Niermeyer, Tyngsboro, MA (US); William Wacks, Sharon, MA (US)

(73) Assignee: Entegris, Inc., Chaska, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 11/434,668

(22) Filed: May 16, 2006

(65) Prior Publication Data
US 2006/0201866 A1    Sep. 14, 2006

Related U.S. Application Data

(62) Division of application No. 10/647,609, filed on Aug. 25, 2003, now Pat. No. 7,056,436, which is a division of application No. 09/796,038, filed on Feb. 28, 2001, now Pat. No. 6,652,749.

(60) Provisional application No. 60/185,991, filed on Mar. 1, 2000.

(51) Int. Cl.
*B01D 27/08* (2006.01)
*B01D 35/153* (2006.01)
*B01D 35/30* (2006.01)

(52) U.S. Cl. .............. 210/232; 210/234; 210/235; 210/446; 210/447

(58) Field of Classification Search ............. 210/232, 210/234, 235, 447, 446
See application file for complete search history.

(56) References Cited

U.S. PATENT DOCUMENTS

| | | | |
|---|---|---|---|
| 1,791,046 A | 2/1931 | Sweeland | 210/130 |
| 3,107,601 A | 10/1963 | Longmire | 99/330 |

(Continued)

FOREIGN PATENT DOCUMENTS

| | | |
|---|---|---|
| DE | 197 17 054 | 11/1998 |
| EP | 0 408 375 | 1/1991 |
| EP | 0 492 627 | 7/1992 |
| EP | 0 616 826 | 9/1994 |

(Continued)

OTHER PUBLICATIONS

The Communication and Supplementary Partial European International Search Report dated Mar. 20, 2003.

*Primary Examiner*—Thomas M Lithgow
(74) *Attorney, Agent, or Firm*—Nields & Lemack

(57) ABSTRACT

Fluid separation assembly that allows easy and fast change-out even in confined spaces, and also minimizes or eliminates leakage during change-out. A fluid separation unit having a housing containing separation means, the housing having an inlet and an outlet spaced from the inlet, each including a fitting for attachment of the housing to a manifold or other device allowing fluid communication through the separation means to a point of use is provided. The fittings are designed for quick connect/disconnect, and for minimal or no leakage. The fittings may be on opposite ends, with top and bottom fittings of different configurations, thereby ensuring proper installation of the assembly. The particular medium to be separated is not particularly limited, and can include slurries, fluids including water, and pre-loaded chromatography columns.

5 Claims, 14 Drawing Sheets

U.S. PATENT DOCUMENTS

| | | | |
|---|---|---|---|
| 3,388,801 A | 6/1968 | Boyd et al. | 210/234 |
| 3,399,776 A | 9/1968 | Knuth | 210/234 |
| 3,519,133 A | 7/1970 | Broering | 210/232 |
| 3,595,397 A | 7/1971 | Abos | 210/232 |
| 3,628,662 A | 12/1971 | Kudlaty | 210/136 |
| 3,802,564 A | 4/1974 | Turman | 210/134 |
| 4,381,871 A | 5/1983 | Dopyera et al. | 285/261 |
| 4,404,103 A | 9/1983 | Drath | 210/446 |
| 4,416,775 A | 11/1983 | Halbich et al. | 210/236 |
| 5,022,986 A | 6/1991 | Lang | 210/94 |
| 5,108,598 A | 4/1992 | Posner | 210/232 |
| 5,256,285 A | 10/1993 | Tomita et al. | 210/234 |
| 5,342,518 A | 8/1994 | Posner et al. | 210/232 |
| 5,397,462 A | 3/1995 | Higashijima et al. | 210/136 |
| 5,397,468 A | 3/1995 | Chomka et al. | 210/232 |
| 5,399,263 A | 3/1995 | Chomka et al. | 210/257.1 |
| 5,560,824 A | 10/1996 | Sann et al. | 210/234 |
| 5,601,710 A | 2/1997 | Yoon et al. | 210/232 |
| 5,651,887 A | 7/1997 | Posner et al. | 210/232 |
| 5,725,623 A | 3/1998 | Bowerman et al. | 55/490 |
| 5,925,025 A | 7/1999 | Weilbacher et al. | 604/317 |
| D423,081 S | 4/2000 | Niermeyer | D23/209 |
| 6,068,770 A | 5/2000 | Niermeyer et al. | 210/321.6 |
| 6,277,277 B1 * | 8/2001 | Jacobi et al. | 210/240 |
| 6,652,749 B2 | 11/2003 | Stankowski et al. | 210/232 |
| 7,056,436 B2 | 6/2006 | Stankowski et al. | 210/232 |

FOREIGN PATENT DOCUMENTS

| | | |
|---|---|---|
| EP | 0 269 054 | 6/1998 |
| EP | 0 887 100 | 12/1998 |
| EP | 1 057 493 | 12/2000 |
| GB | 2 314 516 | 1/1998 |
| JP | 08-052465 | 2/1996 |
| WO | 93/16315 | 8/1993 |

* cited by examiner

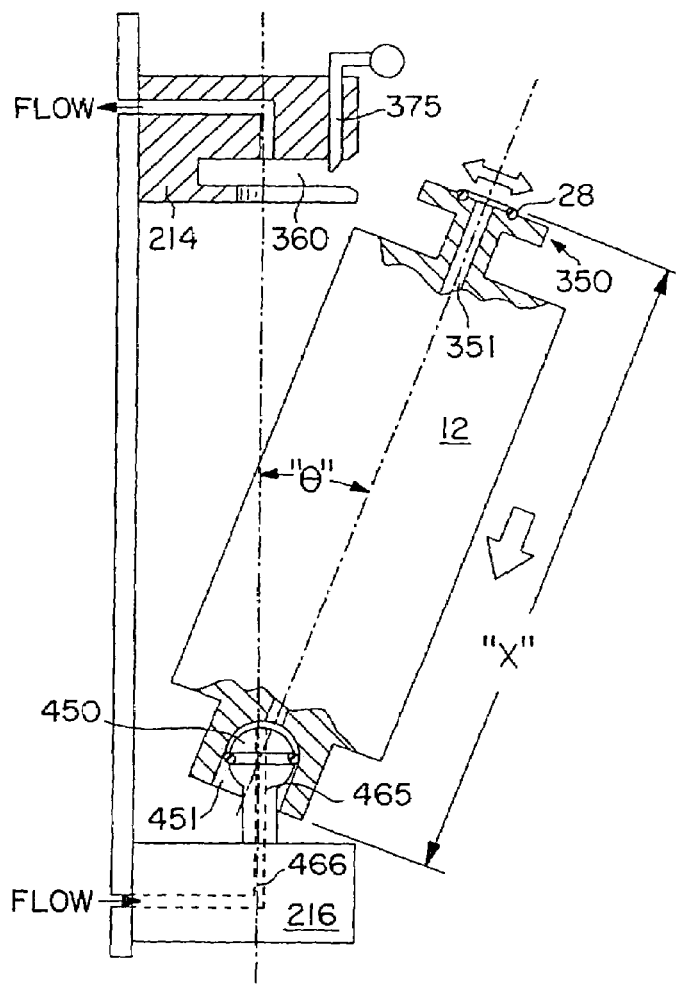
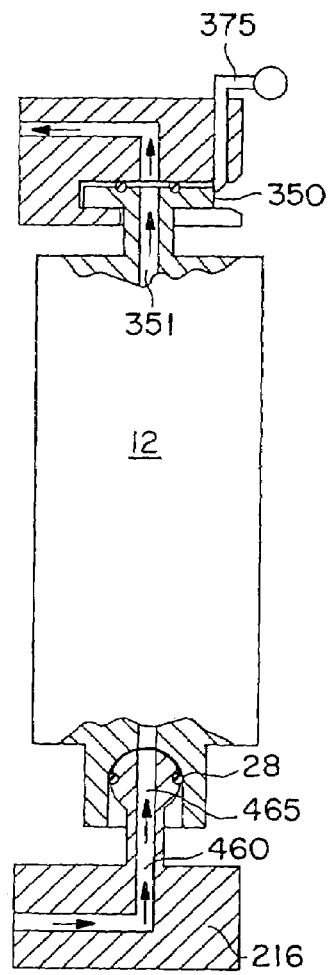
FIG. 10
FIG. 10a

DISPOSABLE FLUID SEPARATION DEVICE AND MANIFOLD ASSEMBLY DESIGN WITH EASY CHANGE-OUT FEATURE

This application is a Divisional of U.S. patent application Ser. No. 10/647,609 filed on Aug. 25, 2003 now U.S. Pat. No. 7,056,436, which is a Divisional of U.S. patent application Ser. No. 09/796,038 filed on Feb. 28, 2001 (now U.S. Pat. No. 6,652,749 issued Nov. 25, 2003), which claims priority of U.S. Provisional Application No. 60/185,991 filed on Mar. 1, 2000, the disclosures of which are incorporated herein by reference.

BACKGROUND OF THE INVENTION

Fluid separation units with fittings may be installed in small spaces that make it very difficult to change out the filter unit. For example, it can be difficult to turn a fitting during installation and removal in a confined space. Even a quick disconnect fitting can be awkward and difficult to manipulate in the spaces typical in industrial filtration applications. Conventional fittings require that there be sufficient space to allow the operator's hands to manipulate the fitting. In addition, there is generally excess tubing, which allows the fittings or quick disconnects to be removed. There also may be additional tubing present to allow the filter unit to be removed from its installed position to a location with room enough that the fittings/quick disconnects can be removed easily. However, moving tubing around is very undesirable because tubing can be easily damaged, and contamination adhering to the inside surface of tubing walls may be dislodged into the fluid. Conventional disposable filters are also time consuming to change due to cumbersome fittings. Also, filters often require extra space above and/or below to allow vertical movement for removal, and space is a premium.

Another problem associated with conventional disposable fluid separation devices is leakage during change-out. Since the chemicals used in a particular process may be hazardous, any leakage is undesirable, both from an environmental standpoint and in terms of operator safety. Similarly, tubing associated with the device can leak or drip during change-out, also potentially resulting in a hazardous condition.

It is therefore an object of the present invention to provide a removable fluid separation assembly that can be installed in a confined space and readily connected and disconnected.

It is a further object of the present invention to provide a removable separation assembly that includes fittings that allow installation with one easy motion and do not require that each fitting be individually connected.

It is yet a further object of the present invention to provide a separation assembly that includes dripless connections, preventing leakage during change-out.

It is still another object of the present invention to provide a separation assembly that minimizes or eliminates air entrapment during change-out.

It is a still further object of the present invention to provide a separation assembly with oriented connection, preventing incorrect installation of the assembly.

SUMMARY OF THE INVENTION

The problems of the prior art have been overcome by the present invention, which provides a fluid separation assembly that allows easy and fast change-out even in confined spaces, and also minimizes or eliminates leakage during change-out. According to a preferred embodiment of the present invention, a fluid separation unit having a housing containing separation means, the housing having a first end and a second end spaced from the first end, each of said first and second ends including a fitting for attachment of the housing to a manifold or other device allowing fluid communication through the separation means to a point of use is provided. The fittings are designed for quick connect/disconnect, and for minimal or no leakage. The top and bottom fittings may be of different configurations, thereby ensuring proper installation of the assembly. The particular medium to be separated is not particularly limited, and can include slurries, fluids including water, and pre-loaded chromatography columns.

BRIEF DESCRIPTION OF THE DRAWINGS

FIG. 10 is a cross-sectional side view of a separation unit being installed in a further embodiment of the present invention;

FIG. 10a is a side view of the unit of FIG. 10 in an installed position;

DETAILED DESCRIPTION OF THE INVENTION

Figure 9:
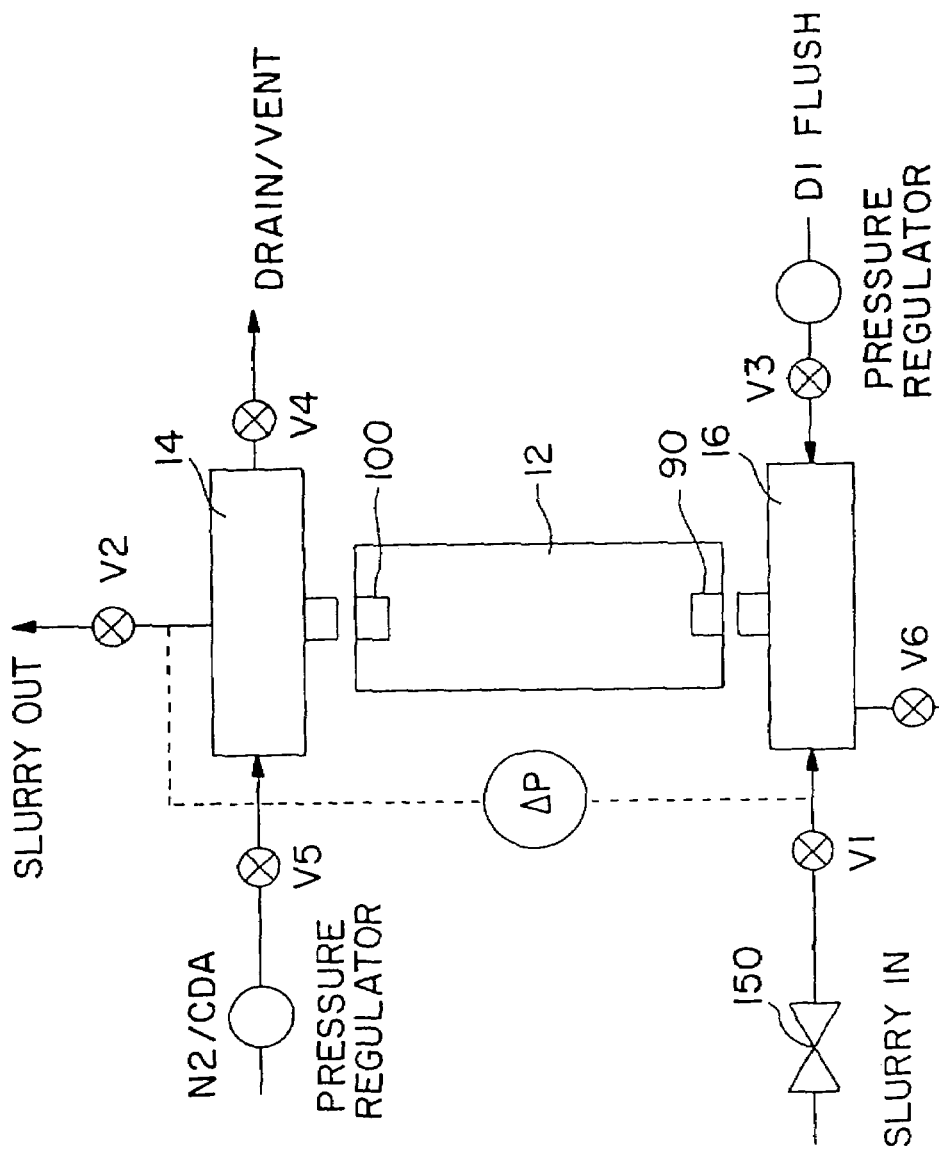
FIG. 9 is a schematic representation of a separation system in accordance with an embodiment of the present invention.

FIG. 9 shows a schematic of a typical fluid separation system in which the present invention may be applied. Those skilled in the art will appreciate that the separation systems of the present invention include filters, purifiers, concentrators and contactors (e.g., degassers and ozonators). For purposes of illustration, the separtions systems will be exemplified by filters, although the present invention is not limited thereto. A filter 12 is shown having an inlet end 90 and an outlet end 100 (these could be reversed), each for respective connection to lower and upper manifolds 16, 14. A nitrogen/clean dry air line is used to purge the filter 12. A deionized water (DI) line is used to flush the filter 12. Suitable preferably air-actuated valves V1-V6 are appropriately positioned as shown. For filter change-out, the manual shut-off valve 150 on the inlet line is closed, and the filter 12 is purged with nitrogen or clean dry air. The filter 12 is then flushed with DI water, purged again with nitrogen or clean dry air, and the filter 12 is removed from the manifolds and replaced. For start-up, after the new filter is installed, it is flushed with DI water, purged, and the manual shut-off valve 150 is opened. The filter 12 is primed with the fluid of choice and ready for use. It will be understood by those skilled in the art that the foregoing procedure is illustrative only; other start-up and change-out procedures could be used with the filter assembly of the present invention.

Figure 1:
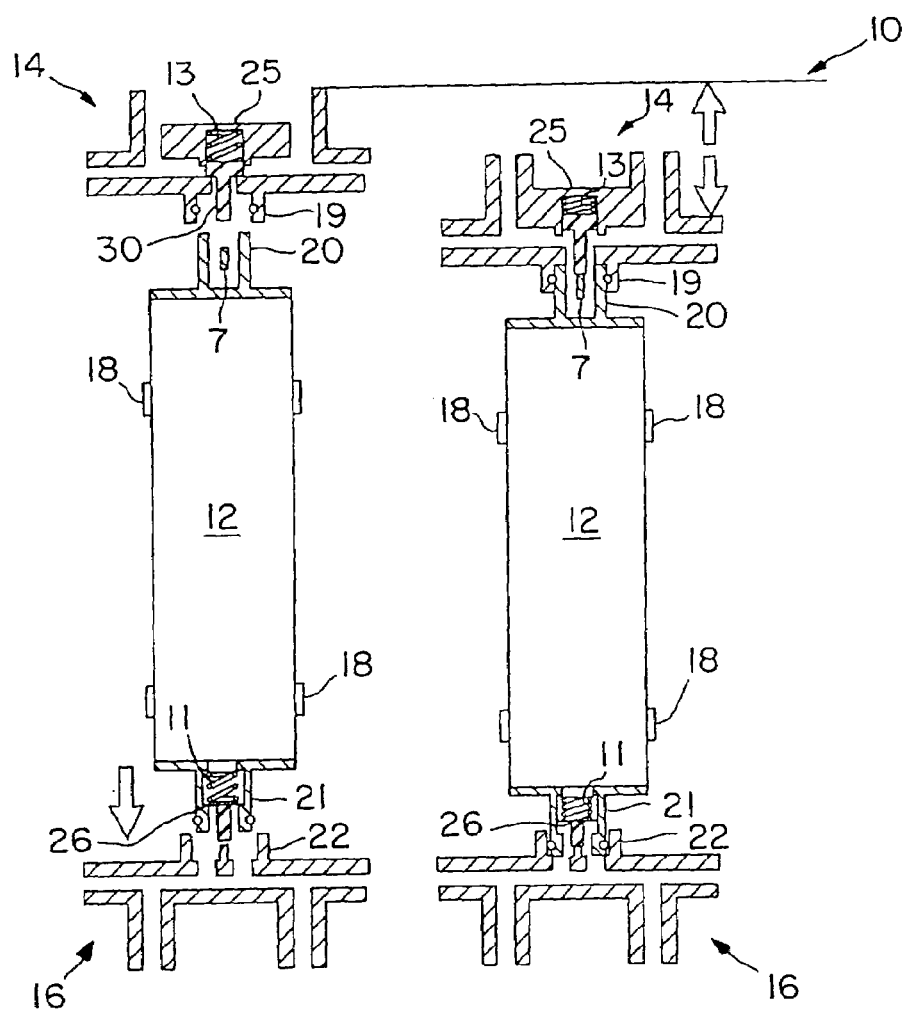
FIG. 1 is a cross-sectional representation of a separation unit in accordance with a first embodiment of the present invention.

Turning now to FIG. 1, there is shown a manifold 10 housing one or more separation units, which in the embodiment shown, are filter units 12 (two shown). Each filter unit 12 is adapted to be connected to a top manifold 14 and a bottom manifold 16. Those skilled in the art will appreciate that although manifolds are illustrated, other means for attaching each filter unit to the system and providing fluid communication into and out of the filter units can be used. For convenience, however, the ensuing description will refer to manifolds. Preferably the manifolds are independent, which will allow for separate changing of each filter unit 12. One or more of the manifolds may include pressure transducers (not shown) or other sensors for monitoring the conditions of the process. The filter units 12 may include one or more guide blocks 18 to facilitate mounting of the units in a module.

The filter units 12 may be completely disposable, or may comprise a reusable housing having a disposable inner cartridge. In the embodiment shown in FIG. 1, the first (top) end of each filter unit 12 has a male fitting or coupling 20, preferably centrally located (with respect to the housing of said filter 12) and preferably cylindrical, for attachment to upper manifold 14. Similarly, the second (bottom) end of each filter unit 12, which is spaced from and preferably opposing the first end, has a fitting or coupling 21, also preferably centrally located, for attachment to receiver 22 on lower manifold 16. At least one of the manifolds 14, 16 is movable between a first disengaged position, shown as the left-hand manifold 14 in FIG. 1, to a second engaged position, shown as the right-hand manifold 14 in FIG. 1. In the first disengaged position, receiver 19 on manifold 14 is disengaged from the coupling 20 of the filter 12. The first disengaged position of manifold 14 is high enough (i.e., sufficiently spaced from the lower manifold 16) in the module such that the filter 12 can be lifted off (vertically, in the direction toward upper manifold 14) of lower manifold 16 and removed. In the second engaged position, coupling 20 is received by receiver 19, engaging the filter unit 12 in place in the module. Although both the upper manifold 14 and lower manifold 16 could be movable, preferably one is movable and the other is stationary in this embodiment.

In a preferred embodiment of the assembly illustrated in FIG. 1, each upper manifold 14 contains a valve 25 that is actuated by engagement of the filter unit 12 with the manifold 14, and more specifically, by engagement of the coupling 20 with the manifold 14. Upon attachment of the filter unit 12 to the manifold 14, the valve 25 is forced open by contact with an actuating member 7 in the coupling 20, allowing fluid communication between the filter unit 12 and the manifold 14. In the embodiment shown, the opening of the valve 25 is caused by contact between the actuating member 7 in coupling 20 and the valve stem 30, which forces the valve in the vertical direction (as depicted in FIG. 1), unseating the valve and allowing fluid to flow past it. When the filter unit 12 is removed from the manifold 14, valve spring 13 biases the valve 25 back to its seated, closed position, preventing leakage from the manifold 14.

Also in a preferred embodiment of the assembly illustrated in FIG. 1, each filter unit 12 includes a valve 26 that is actuated upon engagement of the filter unit 12 with the manifold 16. Upon attachment of the filter unit 12 to the manifold 16, the valve 26 is opened by contacting actuating member 29, allowing fluid communication between the manifold 16 and the filter unit 12. When the filter unit 12 is removed from the manifold 16, valve spring 11 biases the valve 26 to its seated, closed position, preventing leakage from the filter unit 12.

Figure 2A:
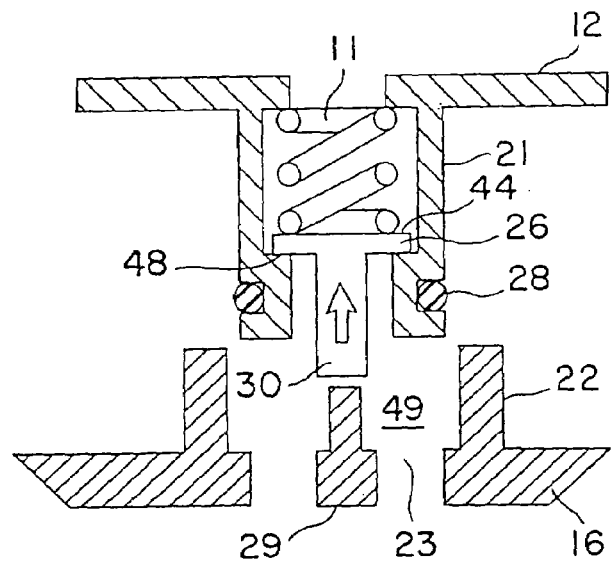
FIG. 2a is a cross-sectional view of a portion of the valve of FIG. 1.
Figure 2:
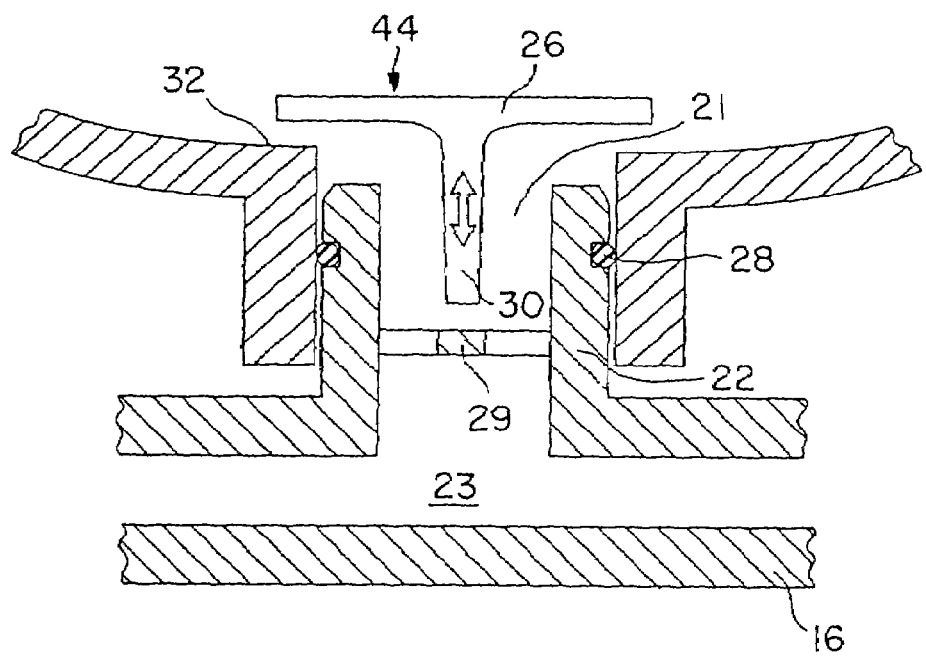
FIG. 2 is a cross-sectional view of a valve for a separation unit in accordance with one embodiment of the present invention.
Figure 3:
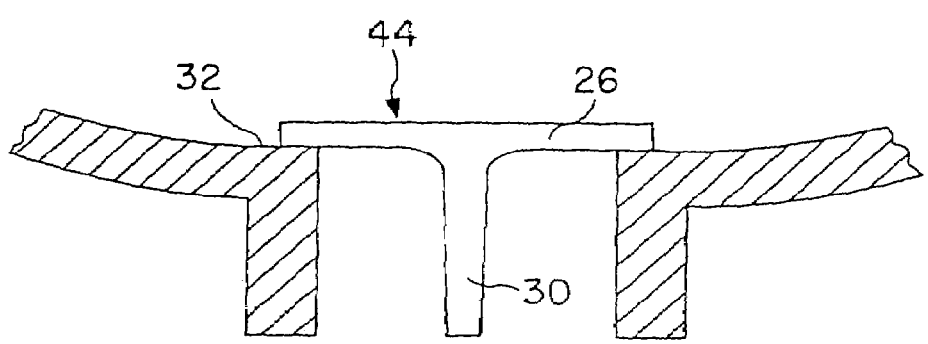
FIG. 3 is a cross-sectional view of a portion of the valve of FIG. 2.

One such suitable valve 26 is shown in greater detail in FIG. 2. Lower manifold 16 includes a fluid passageway 23 providing fluid communication to (or from) filter unit 12. The manifold 16 has a preferably cylindrical projection 22 which receives a corresponding receiving end 21 of filter unit 12 whose inside diameter is greater than the outside diameter of projection 22. The projection 22 (and/or the receiving end 21) has means for creating a sealed fit with the filter unit 12, such as an O-ring. 28. A stationary valve actuator 29 is positioned in manifold 16 such that attachment of the filter unit 12 to the manifold 16 causes the valve stem 30 of T-shaped (in cross-section) valve 26 to engage the actuator 29, forcing the valve in the vertical direction as depicted by the arrow in FIG. 2, allowing fluid to flow about the valve 26 and into the filter unit 12. A spring or the like (not shown) preferably seats on the upper surface 44 of the valve 26, biasing the valve 26 towards its closed position where it seats against the base 32 of the housing or filter 12. In a bottom opening, one can rely upon gravity, however it is preferred to use some other device to assist in the closure. When the filter unit 12 is disengaged from the manifold 16, the valve 26 seals against the housing of the filter unit 12 at 32 as shown in FIG. 3, preventing fluid flow between the manifold 16 and the filter unit 12, and preventing leakage out of the filter unit 12. Those skilled in the art will appreciate that the configuration of the attachment between the manifold 16 and the filter unit 12 is not critical; for example, the fittings could be reversed, with the manifolds being inserted internally into the projections on the filter unit 12. Similarly, since the filter unit 12 is connected to a manifold at an inlet and an outlet, the inlet can have a different connection from the outlet.

FIG. 2a shows greater detail of the design of the valve 26 located in receiving end 21 of filter unit 12, which is received by a corresponding recess 49 in manifold 16. Spring 11 is illustrated biasing the valve 26 towards its sealed position against shoulder 48 of the receiving end 21. O-ring 28 seals the end 21 in the recess 49 of the manifold 16. Actuator 29 is positioned to engage the valve stem as in the embodiment of FIG. 2, to move the valve in the direction of the arrow and unseat it from shoulder 48, allowing fluid to flow about the valve.

Figures 4, 4A:
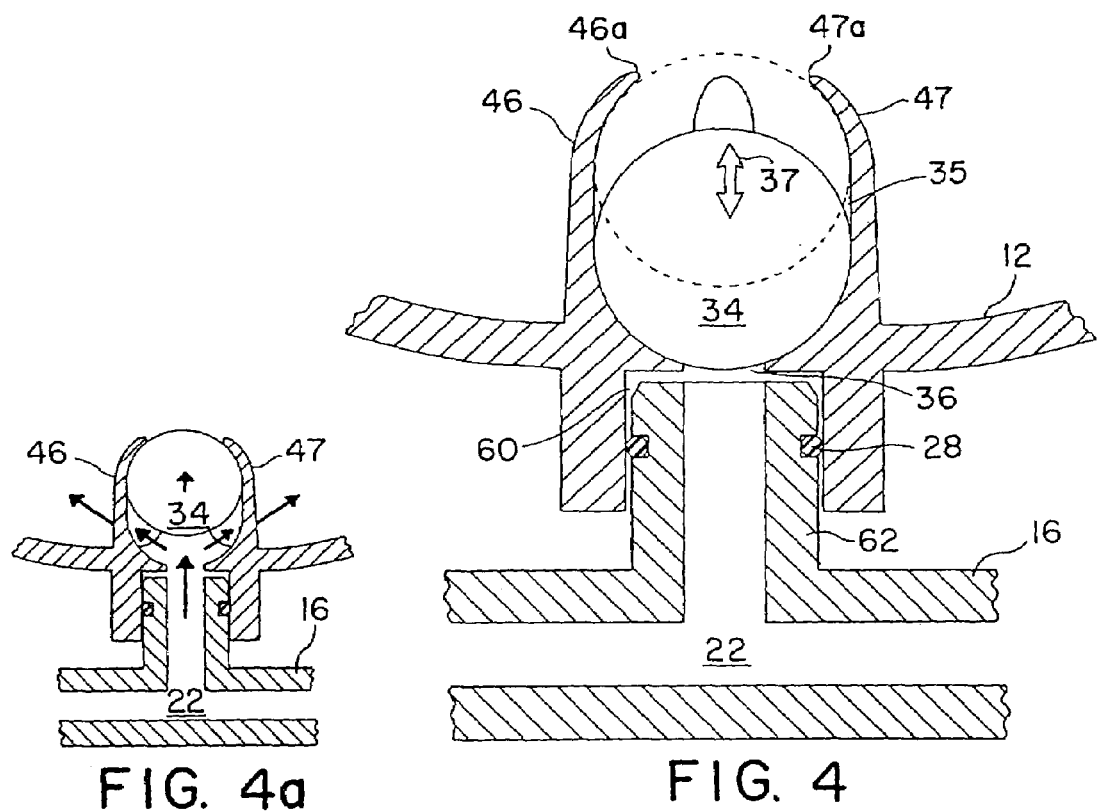
FIG. 4 is a cross-sectional representation of a valve for a separation unit in accordance with another embodiment of the present invention.
FIG. 4a is a cross-sectional view of a portion of the valve of FIG. 4.
Figure 4B:
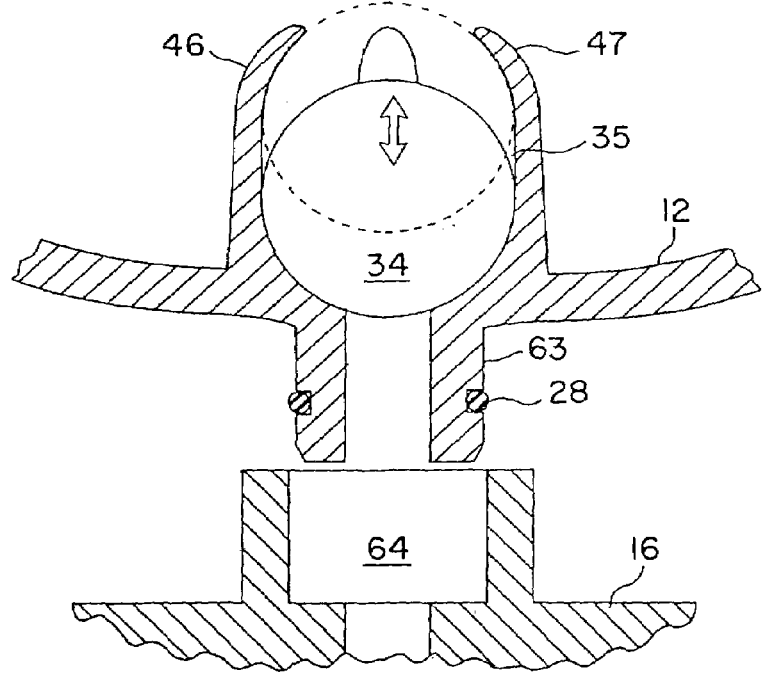
FIG. 4b is a cross-sectional view of another embodiment of the valve of FIG. 4.

FIG. 4 illustrates a second embodiment of the filter unit valve for creating a dripless, rapid disconnect filter assembly. The valve in this embodiment is a ball valve, wherein a spherical member 34 having a density greater than the density of the fluid is housed in a cavity 35 formed in filter unit 12. The cavity is defined in part by at least two spaced opposing arms 46, 47 which converge at their free ends as shown, so that the space between their free ends is smaller than the diameter of the spherical member 34, thereby containing the spherical member 34 and preventing the spherical member 34 from escaping from the cavity 35. Preferably there are two pair of spaced opposing arms. More specifically, the free end of each arm preferably terminates in facing ends 46a, 47a such that the distance between the ends on opposing arms is smaller than the diameter of spherical member 34, thereby providing a stop and limiting the vertical movement of spherical member 34 in cavity 35. A fluid passageway 36 is provided below spherical member 34, providing fluid communication to fluid path 22 of manifold 16. As the fluid flows from manifold 16 into passageway 36, it exerts a pressure on spherical member 34, causing spherical member 34 to travel in the direction of arrow 37 in the cavity 35 and assume the open position shown with phantom lines in FIG. 4, and shown in greater detail in FIG. 4a. Due to the geometry of the cavity 35, with the spherical member in the open, phantom-line position, fluid is allowed to flow around the spherical member 34 and enter the filter unit 12 (FIG. 4a). However, when the fluid flow from the manifold 16 stops, the spherical member 34 returns to the closed position, disrupting the fluid communication between passageway 36 and cavity 35 and preventing fluid from escaping into fluid passageway 36 and leaking out of the filter unit 12. The filter unit 12 can now be removed from the manifold without leakage. Those skilled in the art will appreciate that although a spherical member 34 is preferred, other shapes may be suitable provided the member seals in its closed position and can be moved to its open position by the pressure exerted by the fluid flowing from the manifold. The filter unit 12, which is preferably constructed of a disposable material, seals onto manifold 16 by any suitable means. FIG. 4 shows a recess or socket 60 formed in filter unit 12, shaped to receive male end 62 of manifold 16. Annular O-ring 28 in the end 62 ensures a seal. FIG. 4b shows an alternative embodiment where the male end coupling 63 is on the filter unit 12 and is received by socket 64 in the manifold 16. Annular O-ring 28 is shown placed in the coupling 63 is this embodiment. Those skilled in the art will appreciate that in any embodiment, more than one O-ring may be used, or some other sealing device may be used instead or together with the O-ring(s).

Figure 5A:
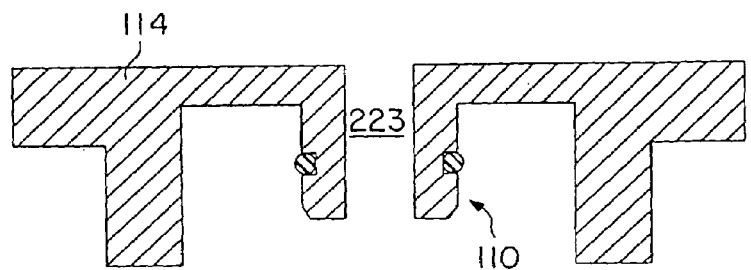
FIG. 5a is a cross-sectional view of the upper fitting of the valve of FIG. 5.
Figure 5:
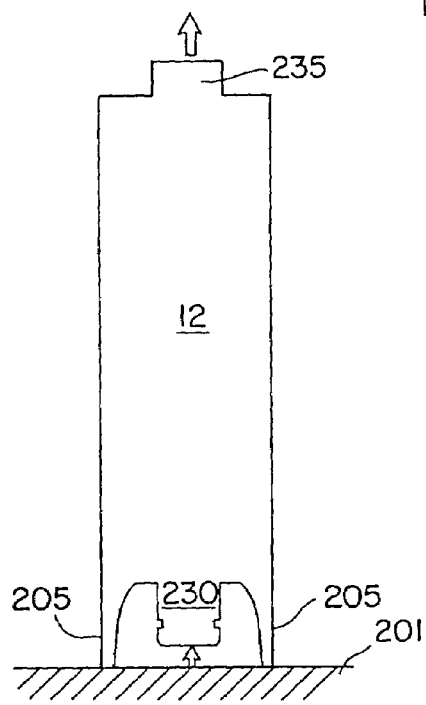
FIG. 5 is a cross-sectional representation of a separation unit in accordance with another embodiment of the present invention.
Figure 5B:
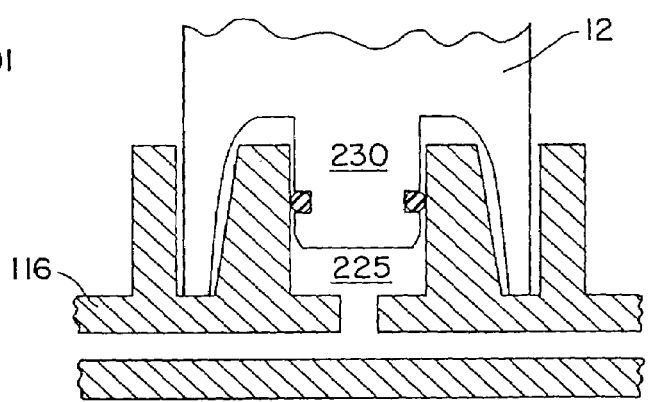
FIG. 5b is a cross-sectional view of the lower fitting of the valve of FIG. 5.

Since the proper orientation of the filter 12 may be critical, FIG. 5 illustrates an embodiment of the filter 12 and manifold that prevents improper installation of the filter 12. Thus, upper manifold 114 has a male extension 110 having a fluid pathway 223. The male extension 110 is sealingly received by corresponding recess 235 in the outlet of filter unit 12. Lower manifold 116 has a different configuration than upper manifold 114. For example, FIG. 5a shows lower manifold 116 having a recess 225 to sealingly receive a corresponding male extension 230 of the inlet of filter unit 12. Since the configurations of the inlet and outlet of filter unit 12 are different, the filter unit 12 can be installed only one way in the manifolds 114, 116. Also shown are spaced legs 205 on filter unit 12, which allow the filter unit 12 to stand on its own. Preferably the legs 205 extend below the male extension 230, so that when the filter unit 12 is standing on a substrate 201, the inlet fitting male extension 230 is not exposed to (and contaminated by) that substrate. Suitable valving (not shown) is used in the inlet and outlet to control fluid flow, such as that shown in FIGS. 2 and 2a.

Figure 6:
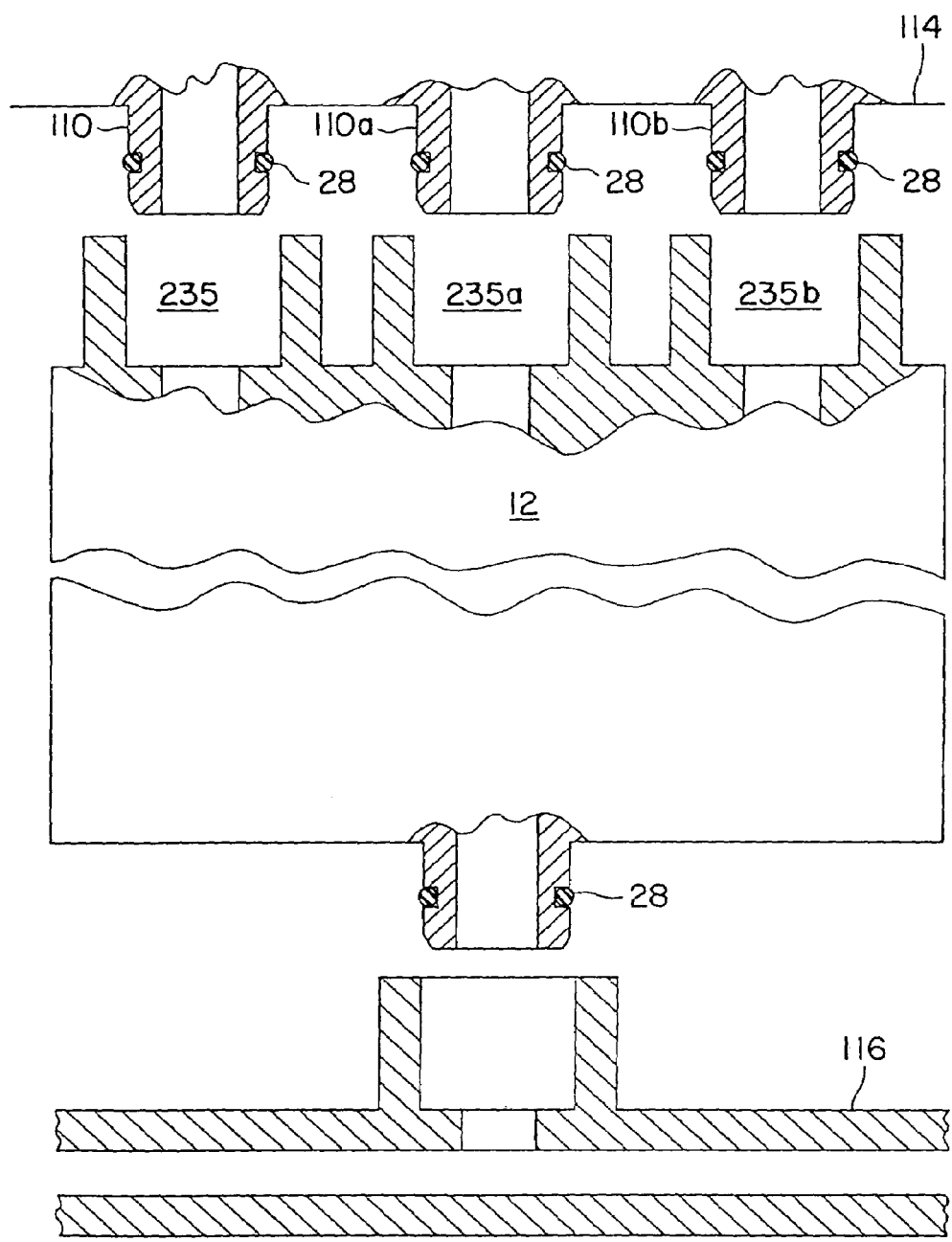
FIG. 6 is a cross-sectional representation of a separation unit in accordance with yet another embodiment of the present invention.

FIG. 6 illustrates an embodiment of the manifold/filter assembly where multiple connections therebetween are made. Male extensions 110, 110a and 110b of upper manifold 114 are sealingly received by corresponding recesses 235, 235a and 235b in the filter unit 12. A single connection between filter unit 12 and lower manifold 116 is shown, thereby again ensuring orientation of the filter unit 12. Although three upper connections and one lower connection are shown, the skilled in the art will appreciate that more or less connections could be used at either end, provided the proper orientation is provided. In addition, one or both of the upper and lower manifolds could be made to move vertically, facilitating installation and removal of the filter unit 12. Suitable valving is used in each connection to control fluid flow.

Figure 7A:
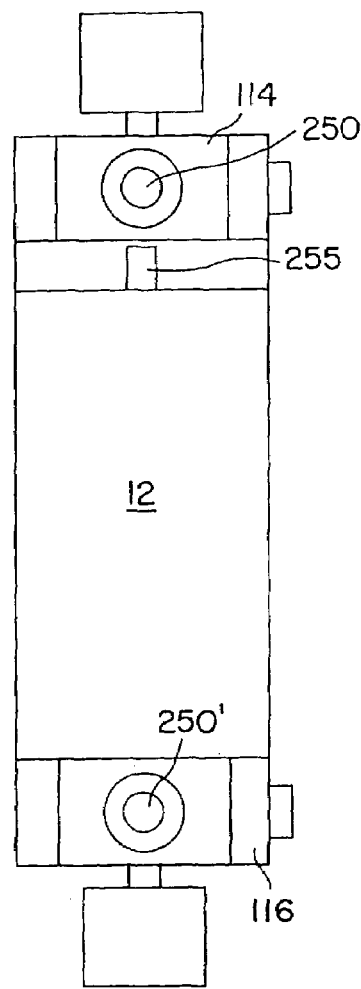
FIG. 7a is a front view of the separation unit of FIG. 7.
Figure 7:
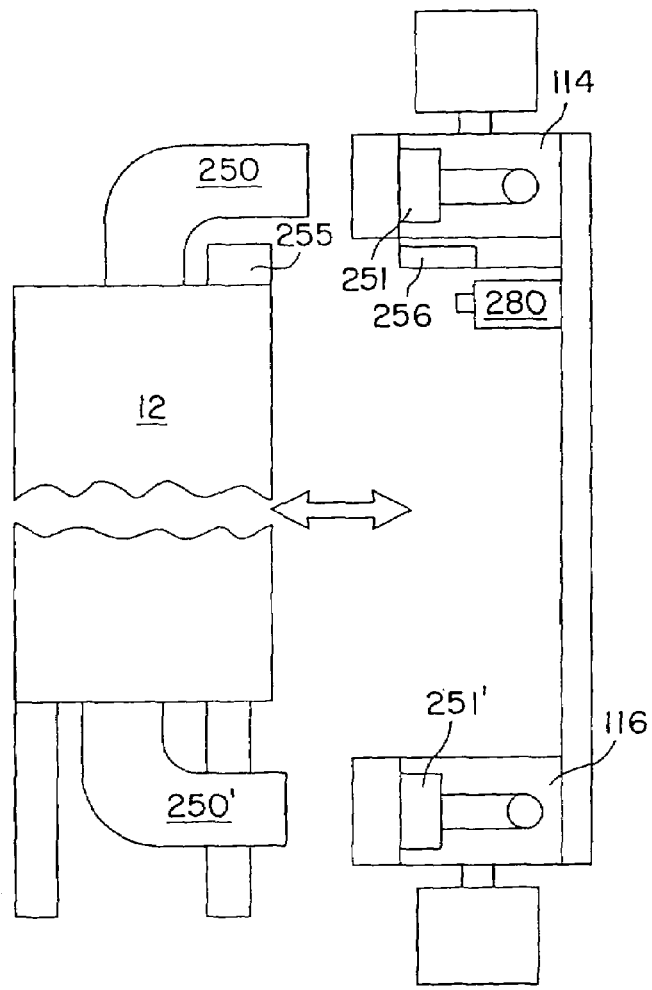
FIG. 7 is a cross-sectional side view of a separation unit in accordance with still another embodiment of the present invention.

FIGS. 7 and 7a illustrate a further embodiment of the present invention. Communication and connection of filter unit 12 to tipper and lower manifolds 114, 116 are made with elbow couplings 250, 250'. Each elbow fits into a correspondingly shaped socket 251, 251' in the respective manifold. An alignment rib 255 can be provided on the filter unit 12 as shown, which slides into a correspondingly shaped alignment slot 256 formed in the upper manifold 114. A similar rib/slot arrangement can be used for the lower manifold 116 as well. This ensures proper alignment of the filter unit 12 as it is slidingly received by the manifolds. Indicating means 280 such as a microswitch can be used to turn off the system (and stop fluid flow) when the filter 12 is removed. A latch mechanism (not shown) or other locking means is used to lock the filter unit 12 to the manifolds when in use, preventing premature disengagement.

Figure 8B:
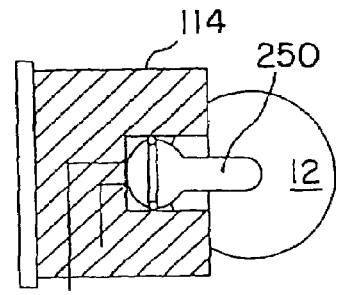
FIG. 8b is a cross-sectional top view of the unit of FIG. 8 shown in the installed position.
Figure 8:
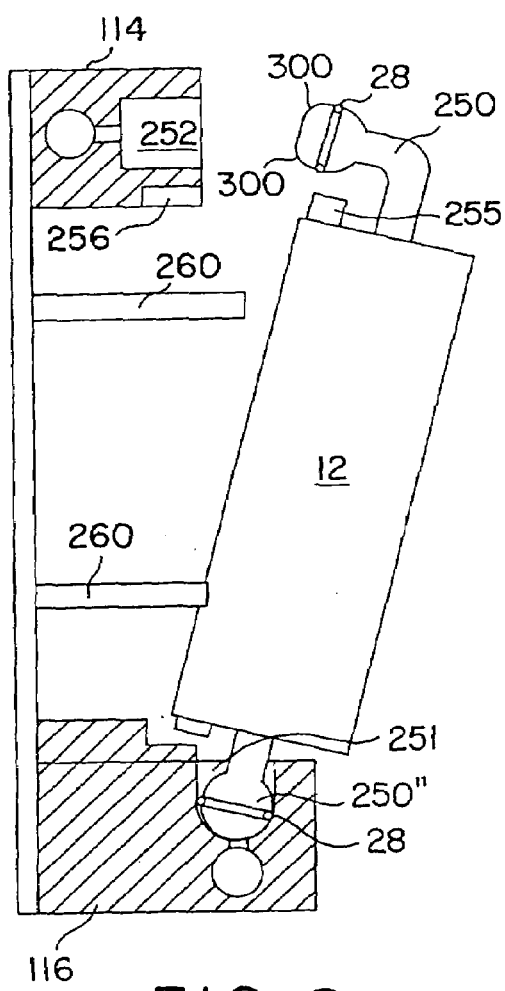
FIG. 8 is a cross-sectional side view of a separation unit in accordance with another embodiment of the present invention, shown being installed in the manifold.
Figure 8A:
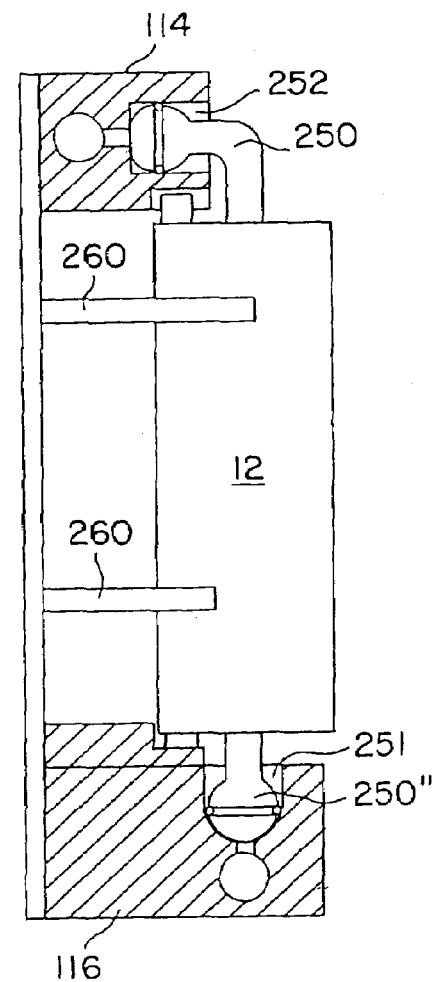
FIG. 8a is a cross-sectional side view of the separation unit of FIG. 8 shown in the installed position.

FIGS. 8, 8a and 8b illustrate an embodiment similar to that shown in FIG. 7, except that only upper coupling or fitting 250 is shaped as an elbow; lower coupling or fitting 250" is a ball design, preferably made of a rigid polyolefin, such as polypropylene, or stainless steel or other metal, depending upon the application. To install the filter unit 12 into the system, the lower fitting 251" is first inserted into lower manifold 116 as shown in FIG. 8. This is accomplished by tilting the filter unit 12 relative to the manifold, as shown. Once the ball fitting 251" is inserted into the corresponding recess 251 in the lower manifold 116, the upper elbow fitting 250 is then inserted into socket 252 in upper manifold 114 as shown in FIG. 8*a*. The elbow fitting 250 can be chamfered such as at 300 to facilitate its entry into socket 251. One or more guides 260 can be used to properly align and orient the filter unit 12. The configuration of the ball design 250" and corresponding socket 251 allows the ball 250" to swivel in the socket 251, thereby providing some "play" as the filter unit 12 is moved from the tilted position of FIG. 8 to the engaged position of FIG. 8*a*. This facilitates installation and removal of the filter device 12 at an angle, without requiring that either manifold 114 or 116 move. The depth of the socket 251 is preferably sufficient to allow movement in the axial (downward) direction to enable the upper fitting to be properly aligned with the upper manifold 114. In addition, since the filter device 12 has a tendency to move in the axial direction (i.e., the direction of flow) when under pressure, the depth of the socket 251 can accommodate this movement as well. Regardless of the particular location of the ball 250" in the socket 251 however, the annular O-ring 28 creates a suitable seal. The diameter of the ball 250" and the length of the socket 251 determines the degree to which the filter unit 12 can be tilted with respect to the axis of fluid flow for installation and removal. Preferably, the filter unit 12 can be tilted at least about 20 degrees away from vertical.

More specifically, with reference to FIG. 10, for filter units having a length (from fitting to fitting, as shown in FIG. 10) in the range of 4-8 inches, the tilt angle range necessary for installation and removal with stationary manifolds is an angle θ of from about 8° to about 15° or greater. For filter units having a length in the range of about 8-18 inches, the tilt angle range is from about 5° to about 13° or greater. For filter units having a length of about 18-40 inches, the tilt angle range is an angle of from about 2° to about 5° or greater.

Figure 8C:
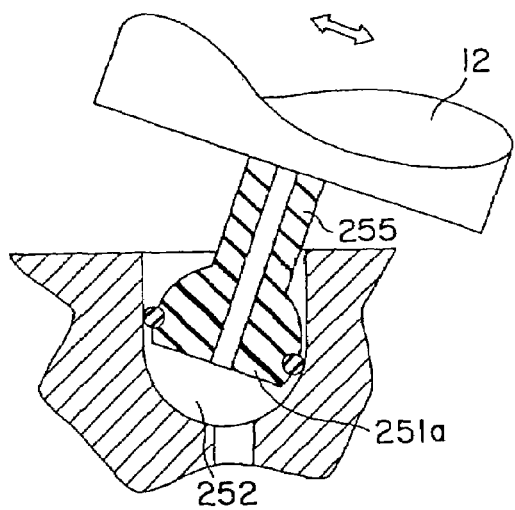
FIGS. 8c, 8d and 8e are cross-sectional views of further embodiments of the fitting in accordance with the present invention.
Figure 8D:
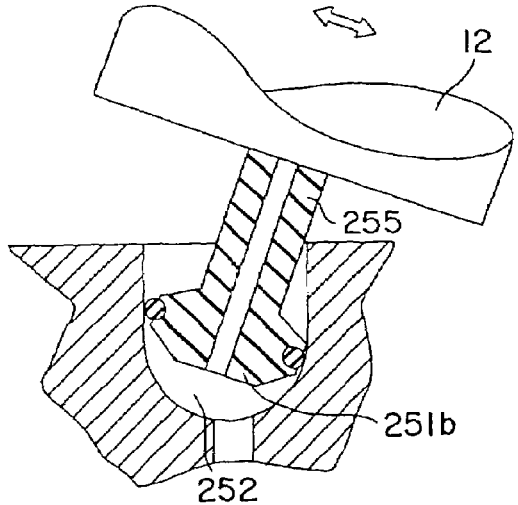
Figure 8E:
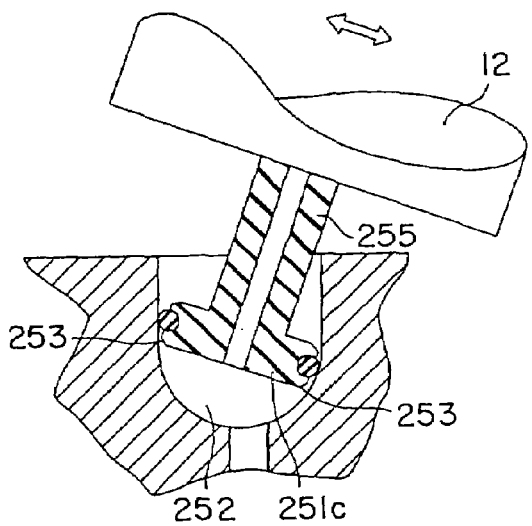
Figure 8F:
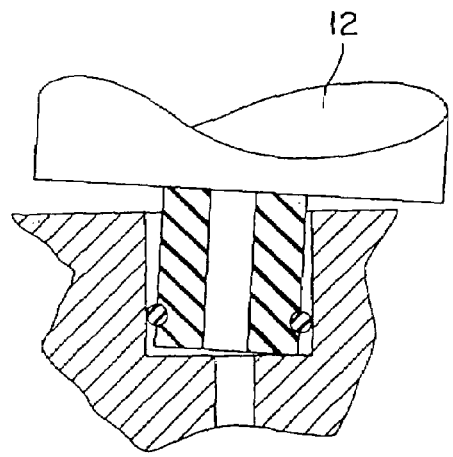
FIG. 8f is a cross-sectional view of a prior art fitting.

FIGS. 8*c*, 8*d* and 8*e* show alternative configurations for the fitting 251. An important factor among the various embodiments is a decrease in diameter of the fitting from a maximum diameter where the fitting engages and seals against the walls of the socket 252, towards the filter housing 12. Also, preferably the fitting is connected to the housing 12 with a neck 255 having a diameter smaller than the maximum diameter of the fitting 251, so that the unit is easily tiltable with respect to the axis of fluid flow and can be readily inserted into (or removed from) the socket 252. These parameters provide the necessary relief to allow the unit to pivot in the socket 252 so it can be connected or disconnected from stationary manifolds. In FIG. 8*c*, the fitting 251*a* includes an elongated neck portion 255 extending from filter unit 12, terminating in a semispherical portion having an O-ring about its portion of maximum diameter to seal in the socket 252. The neck 255, being of smaller diameter than the fitting 251*a*, allows the pivoting action shown. The entry edges of socket 252 can be chamfered (not shown) to facilitate entry of the fitting 251 therein. FIG. 8*d* illustrates a further embodiment of the fitting 251 where a polygonal shape is used. Again, the maximum diameter of the fitting 251*b* is where the fitting engages and seals against the walls of the socket 252. FIG. 8*e* is a further embodiment, where fitting 251*c* has a substantially rectangular shape. Chamfered edges 253 can facilitate entry of the fitting 251*c* into the socket 252. FIG. 8*f* shows a prior art configuration where there is no reduction in diameter of the length of the fitting. As a result, the housing 12 cannot be tilted to a sufficient angle for installation into a stationary manifold.

Figure 10B:
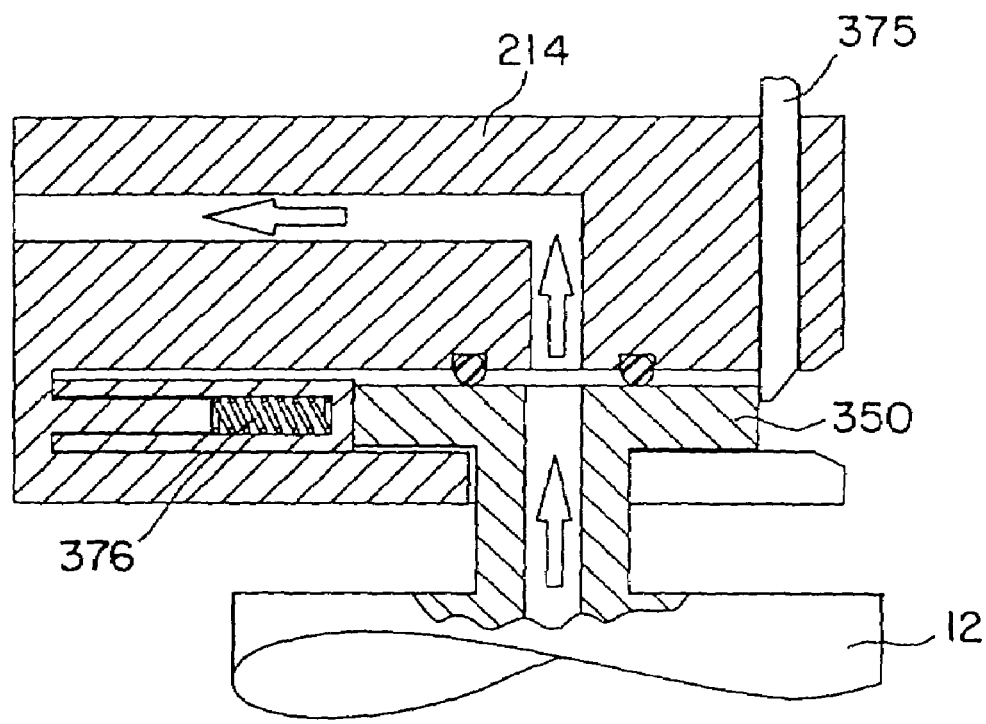
FIGS. 10b and 10c are enlarged view of the latch mechanism of FIG. 10.
Figure 10C:
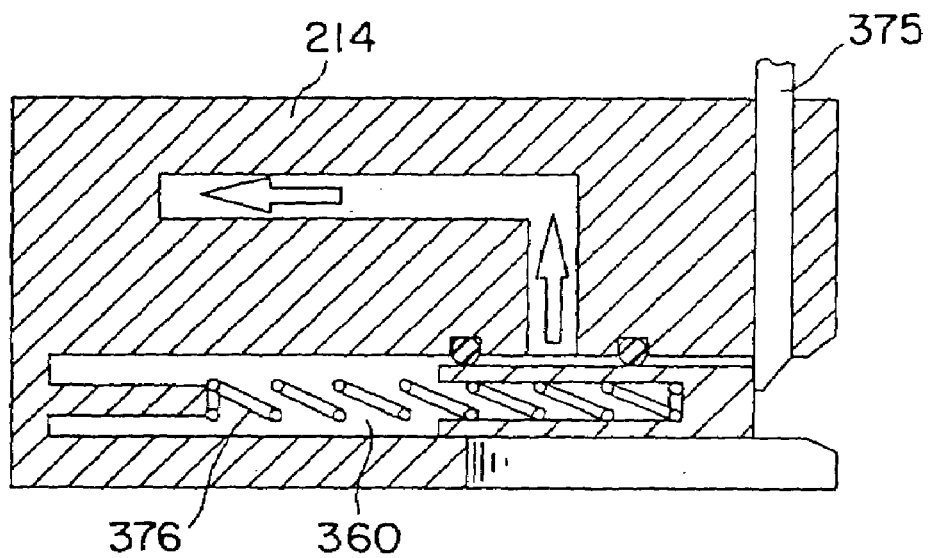
Figure 10D:
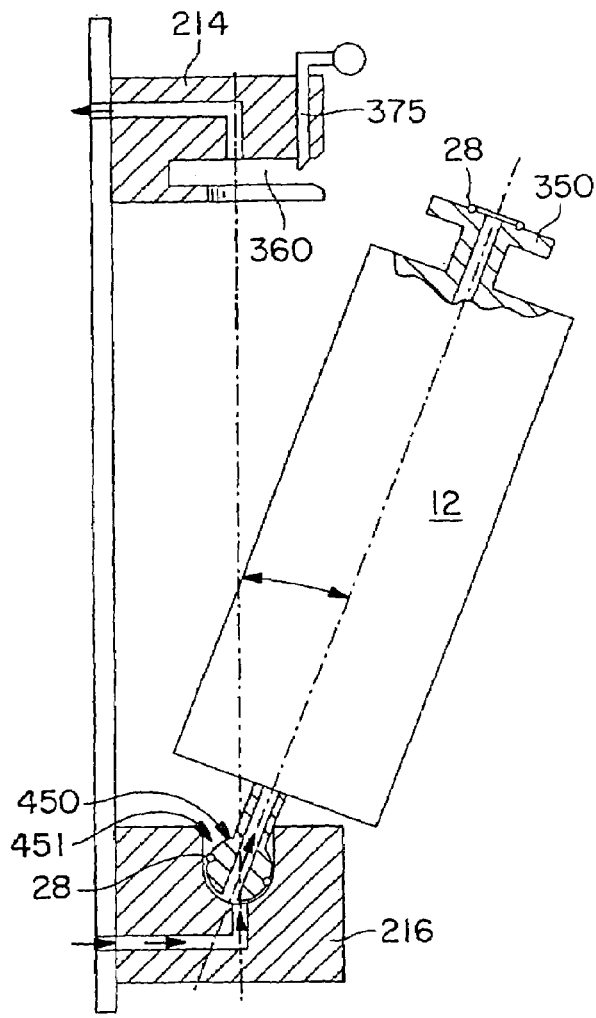
FIG. 10d is a cross-sectional view of a separation unit being installed in a further embodiment of the present invention.
Figure 10E:
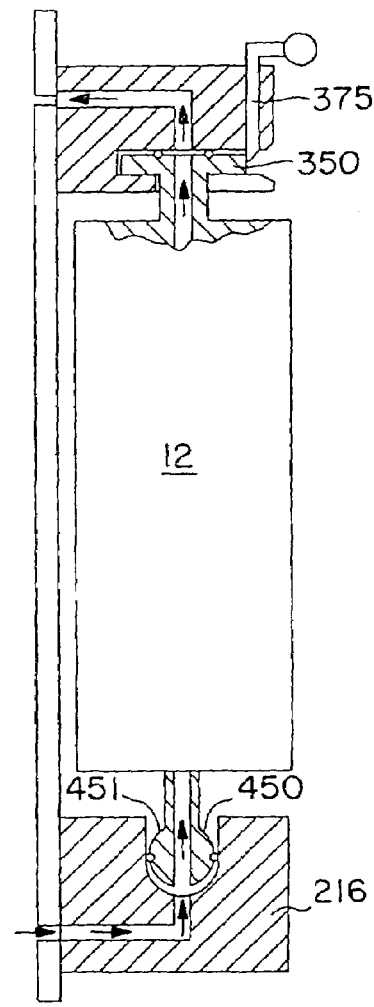
FIG. 10e is a side view of the unit of FIG. 10d in an installed position.

FIGS. 10, 10*a*, 10*d* and 10*e* illustrate further embodiments of the present invention, wherein the upper coupling uses a simple planar face seal and fits into a corresponding slot in the upper manifold 214. The upper coupling 350 is T-shaped in cross-section, with a central passageway 351 allowing for fluid communication between the filter and the manifold 214. An O-ring 28 placed in a groove on the top surface of the coupling 350 can seal in the manifold slot 360. Alternatively, the O-ring 28 can be located in a groove in the slot 360 itself. In the embodiment of FIG. 10 and 10*a*, lower coupling is a swivel similar to that shown in FIG. 8, however the ball 450 is shown as part of the lower manifold 216. The ball 450 is received in recess 451 in the filter assembly 12, which is appropriately dimensioned to enable the tilting shown in FIG. 10 and insertion of the upper T-shaped fitting 350 in the slot 360 of upper manifold 214. Annular O-ring 28 seals about the ball 450 as shown. The ball includes a passageway 465 that extends into manifold 216 for fluid communication between the manifold and the filter 12 when assembled. In the embodiment of FIGS. 10*d* and 10*e*, the ball 450 is placed on the assembly 12 as in FIG. 8, and is received in a recess in the lower manifold 216. The recess 451 is appropriately dimensioned to receive the ball 450, and the space between the upper and lower manifolds (which are preferably stationary) is such to enable the tilting shown in FIG. 10*d* and insertion of the upper T-shaped fitting 350 in the slot 360 of the upper manifold 214. The ball 450 is sealed in the recess such as by an annular O-ring 28. A latch 375 can be used on upper (or lower) manifold 214 to secure the device in place. For example, with reference to FIGS. 10*b* and 10*c*, a spring 376 biases against latch 375 in the uninstalled position of FIG. 10*c*, and biases the fitting 350 against the latch 375 in the installed position of FIG. 10*b*. The free end of the latch 375 can be chamfered as shown, to assist the T-shaped fitting 350 in entering the slot 360. By using the swivel fitting, both the upper and lower manifolds can be stationary. FIG. 10 shows the filter 12 in a tilted (with respect to manifold 214) position, and FIG. 10*a* shows the filter 12 in an engaged position in the manifold 214.

Figure 11:
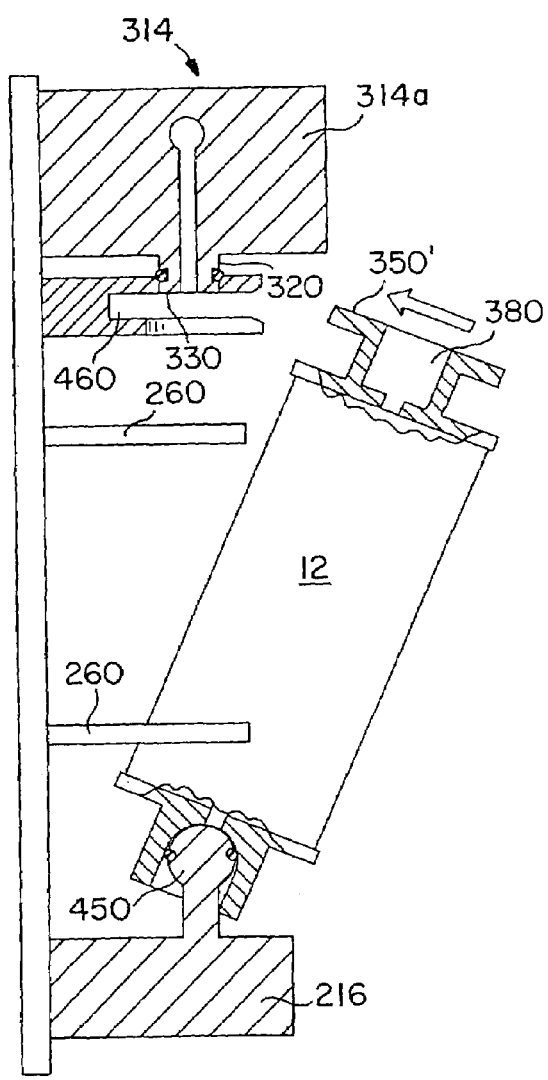
FIG. 11 is a cross-sectional side view of a separation unit being installed in a still further embodiment of the present invention.
Figure 11A:
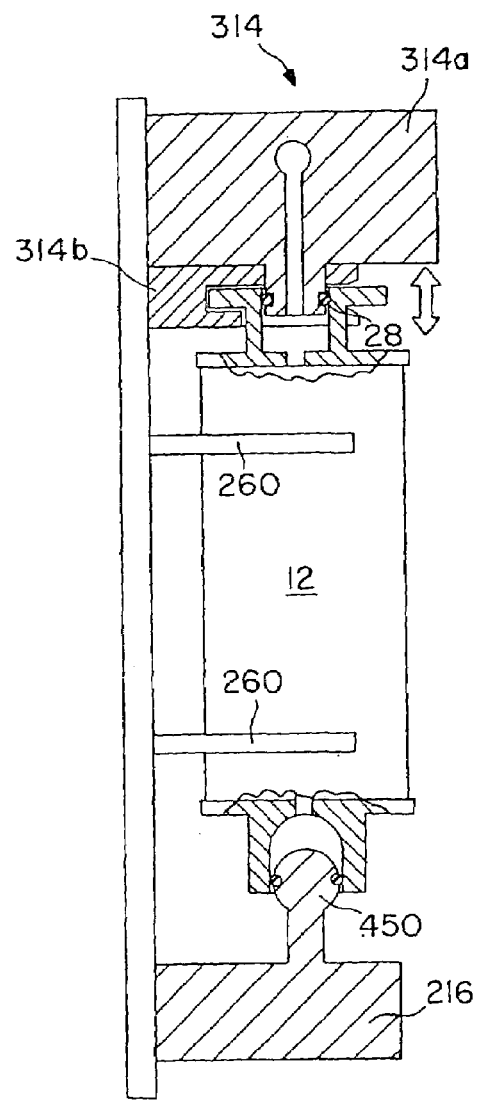
FIG. 11a is a cross-sectional side view of the separation unit of FIG. 11 in an installed position.

FIGS. 11 and 11*a* show a bottom fitting similar to that of FIGS. 10 and 10*a*, with stationary lower manifold 216. However, in this embodiment, the top fitting is connected to a movable manifold portion. Specifically, the upper manifold 314 includes a stationary portion 314*a* and a movable portion 314*b*. The stationary portion 314*a* includes a male extension 320 having a fluid passageway therein. The movable portion 314*b* includes a recess 330 that receives the male extension 320, and a slot 460 that receives the upper coupling 350' of the filter assembly 12. The upper coupling 350' includes a recess 380 that receives male extension 320 when the movable portion 314*b* is in its manifold-engaging position as shown in FIG. 11*a*. An annular O-ring about the extension 320 seals in the recess 380. Since in this embodiment the upper manifold has a movable portion, it is not critical that a swivel fitting be used as the lower fitting; other suitable fittings such as that disclosed in the embodiment of FIG. 1 could be used such that the filter assembly is connected without the titling operation shown in FIG. 11.

Figure 12:
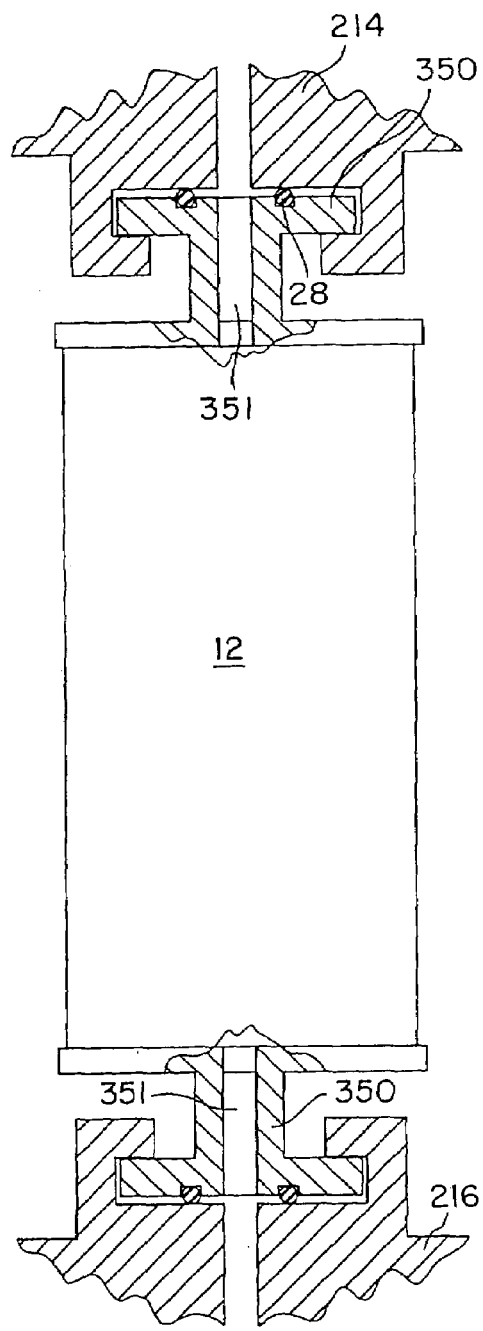
FIG. 12 is a cross-sectional side view of an installed separation unit in accordance with another embodiment of the present invention.

FIG. 12 shows a further embodiment, wherein the fittings on both the top and bottom are similar to the T-shaped design of FIG. 10. The filter 12 slides into the two manifolds virtually simultaneously, and preferably one or both of the upper and lower manifolds is movable in the axial direction to account for variation in filter length amongst various filters and allow connection and engagement of the filter.

Figure 13:
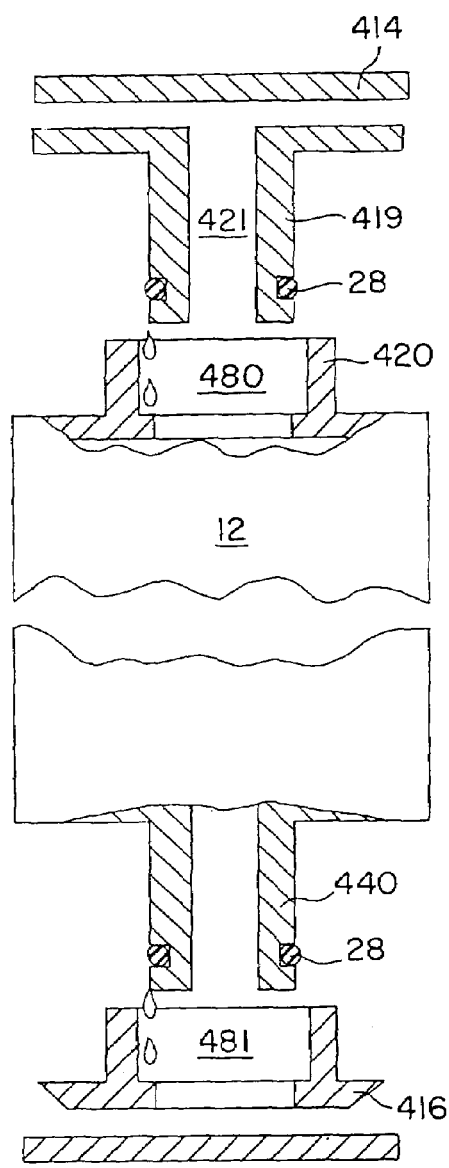
FIG. 13 is a cross-sectional side view of yet another embodiment of the present invention.

The embodiment of FIG. 13 shows a stationary upper manifold having a male extension 419, defining a passageway 421. The extension 419 is received by a correspondingly-shaped recess 480 in extension 460 of filter 12. Annular O-ring 28 creates a seal within the recess 480 when the extension 419 is engaged therein. The opposite end of filter 12 includes an extension 440 that seals in recess 481 of the lower manifold 416. Annular O-ring 28 seals in the recess 481 when the extension 440 is engaged therein.

What is claimed is:

1. A separation unit and manifold assembly, said separation unit comprising a housing having at least one first fitting comprising a spherical portion and a stem extending therefrom, at least one second fitting spaced a certain distance from said first fitting, and separation means within said housing between said first and second fittings; said manifold comprising a first portion having a fluid path for fluid communication with said filter through said at least one first fitting, and a second portion having a fluid path for fluid communication with said filter through said at least one second fitting; said at least one first fitting having a portion of maximum diameter located on said spherical portion for sealing engagement with said first portion of said manifold, and having a portion of reduced diameter relative to said maximum diameter located on said stem; said first portion of said manifold including a first recess for receiving said at least one first fitting; said second portion of said manifold including a second recess for receiving said second fitting, whereby the maximum distance between said first and second recesses is greater than the certain distance between said first and second fittings.

2. The separation unit and manifold assembly of claim 1, wherein said first and second fittings have different configurations.

3. The separation unit and manifold assembly of claim 1, wherein said separation means comprises a filter.

4. The separation unit and manifold assembly of claim 1, wherein when said at least one first fitting of said separation unit is inserted into said first portion of said manifold, said separation unit has an orientation of an angle $\ominus$ elative to vertical, and wherein said maximum distance between said first and second recesses of said manifold is sufficient to allow said at least one second fitting of said separation unit to be insertable into said second recess by angling said separation unit relative to said angle $\ominus$.

5. The separation unit and manifold assembly of claim 4, wherein $\ominus$ is zero.

* * * * *